United States Patent
Mays, Jr.

(10) Patent No.: US 6,379,623 B1
(45) Date of Patent: Apr. 30, 2002

(54) SYSTEM FOR USING LUMINESCENT PIEZOELECTRIC TO DETECT BIOLOGICAL AND/OR CHEMICAL AGENTS

(76) Inventor: Robert Mays, Jr., 10707 Pinehurst Dr., Austin, TX (US) 76747

( * ) Notice: Subject to any disclaimer, the term of this patent is extended or adjusted under 35 U.S.C. 154(b) by 12 days.

(21) Appl. No.: 09/614,200

(22) Filed: Jul. 12, 2000

Related U.S. Application Data

(60) Provisional application No. 60/143,375, filed on Jul. 12, 1999.

(51) Int. Cl.[7] .............................................. G01N 21/64
(52) U.S. Cl. ..................................... 422/82.08; 422/91
(58) Field of Search ....................... 436/172; 422/82.08, 422/91; 250/361 R, 484.2, 909

(56) References Cited

U.S. PATENT DOCUMENTS

| | | | |
|---|---|---|---|
| 3,610,926 A | * 10/1971 | Kastner et al. ................ | 250/71 |
| 4,897,541 A | * 1/1990 | Phillips ...................... | 250/227 |
| 4,991,150 A | * 2/1991 | Wixom ........................ | 367/140 |
| 5,399,315 A | * 3/1995 | Paz-Pujalt et al. ............. | 422/56 |
| 5,411,709 A | * 5/1995 | Furuki et al. ................. | 422/91 |
| 5,446,334 A | * 8/1995 | Gaffney ....................... | 310/338 |
| 5,622,868 A | * 4/1997 | Clarke et al. ................. | 436/147 |
| 6,079,252 A | * 6/2000 | Tabler et al. .................. | 73/40 |
| 6,284,546 B1 | * 9/2001 | Bryning et al. ............. | 436/172 |

OTHER PUBLICATIONS

Dobrovol'skii et al. Interaction of Surface Acoustic Waves in A Phosphorbearing Piezoelectric: A New Method for Exciting Electroluminescence. *Sov. Tech. Phys. Lett.* 4(7), Jul. 1978. pp. 303–304, United States of America.

Vigoureux, P. and C.F. Booth. *Quartz Vibrators and Their Applications*. Crown Copyright Reserved, His Majesty's Stationary Office, York House, London, w.c.2, 1950.

* cited by examiner

*Primary Examiner*—Jeffrey Snay
(74) *Attorney, Agent, or Firm*—Kenneth G. Brooks

(57) ABSTRACT

The present invention provides a real-time luminescent piezoelectric detector capable of sensing the presence of biological and chemical agents. This detector includes a free-standing thin film that is driven by a frequency drover to produce light emitted from an edge of the thin film. A surface layer sensitive to the biological or chemical agent to be detected is disposed on the surface of the thin film. In the presence of the biological or chemical agent to be detected, the light emitted from the edge of the thin film structure is altered. A processor capable of determining the presence and/or concentration of the biological or chemical agent in question based on the altered emitted light receives an output representative of the emitted light and outputs the status of the presence and/or concentration of the biological or chemical agent in question.

9 Claims, 3 Drawing Sheets

SYSTEM FOR USING LUMINESCENT PIEZOELECTRIC TO DETECT BIOLOGICAL AND/OR CHEMICAL AGENTS

RELATED APPLICATION

This application claims the benefit of and incorporates by reference U.S. Provisional Application No. 60/143,375 filed on Jul. 12, 1999 entitled Luminescent Piezoelectric Biological/Chemical Agent Sensor by inventor Robert Mays, Jr.

TECHNICAL FIELD OF THE INVENTION

The present invention relates generally to systems and methods of detecting biological and/or chemical agents, and more particularly, a system and method that uses luminescent piezoelectric to detect these biological and chemical agents.

BACKGROUND OF THE INVENTION

Biological and chemical element detection are currently considered to be among the highest priorities to scientific, personal and medical, as well as national security. A significant concern is the inability to even detect the presence or nature of the various chemical or biological agents in a timely manner. This inability seriously impairs the implementation of appropriate responses. Existing detection methods either depend upon on-site sample collection, with the undesirable possibility of exposing or infecting personnel in the case of virile environments, and subsequent, time-consuming/sensitive laboratory analysis; or the use of (quasi-) real-time remote spectroscopic analysis of the surrounding and/or immediate environment which may or may not be directly coupled to or preserving of the element(s) in question. On-site sample collection is difficult, time consuming and expensive. Additionally, this method suffers from the need for large numbers of samples, especially for thinly dispersed (virile) biological agents and/or chemical elements or toxins, and a number of fully equipped virilogical/histrological laboratories near the immediate vicinity for a truly accurate analysis. Even if such facilities are readily available, some agents require days to weeks for unambiguous identification—an unsatisfactory time-frame much too long for many medical/personal and scientific operations. The second approach of using remote spectroscopic (optical) analysis may have an advantage of (quasi-) real-time identification but only works when the agents in question are sufficiently concentrated to yield a detectable signal. This technique is also a high cost solution which will not be affordable for very many large area, multi-unit operations.

It would be desirable to have a system that allows the possibility of a real-time biological/chemical sensor. Furthermore, the need exists for such a sensor that is both small and inexpensive. This would allow distribution to only personnel to be alerted on an individual basis to possible exposure(s) and reactions, and to aid subsequent medical personnel in their post-exposure treatment strategy and/or status monitorings.

This latter need addresses not only the interests of the scientific and laboratory communities, but also immediate needs within the medical and biomedical arenas in the areas of personal prognostic health monitoring.

SUMMARY OF THE INVENTION

The present invention provides a biological and chemical agent detection system and method that substantially eliminates or reduces disadvantages and problems associated with previously developed systems and methods.

More specifically, the present invention provides a system for detecting chemical and biological agents using luminescent piezoelectrics.

The present invention includes a free-standing thin film EL phosphor onto which a biological and/or chemical active surface layer has been deposited. The EL film is electronically or mechanically excited to, or near resonance, and the edge emitted light intensity is measured. Upon exposure to the appropriate agent, the surface layer either increases in mass, decreases in mass, changes it surface tension, changes its viscosity, etc., thereby changing the resonators response to the driving frequency. This will either be detected as a change in the emitted light intensity or a shift in the driving frequency to achieve the same light intensity thereby indicating the presence and/or concentration of the agent.

Other important embodiments examine changes in the surface layer's optical coupling to the resonator (e.g., through gratings or other optical structures fabricated on the free-standing film surface) thereby increasing/decreasing the amount of light scattered out of the flat surface of the thin film waveguide and/or providing the spectral content/signature of the emitted light/specimen.

Other designs may include the use of an atomic stylus or tip configuration as used in atomic force microscopes to enhance/amplify the sensitivity of the sensor by an order of magnitude or more.

Another embodiment may integrate micro-sensors can be integrated directly onto the edges or surfaces where the signal or light emission occurs in order to provide tremendous increases in the sensing capability as compared to a strictly visual sensing.

In yet another embodiment, combinations of nanometer-micron thick phosphor and/or film stacks (including porous structures/materials) may be used to provide a color discriminator between an uncontaminated and contaminated condition (e.g. green emission implies safe, but red emission implies danger).

The present invention provides an important technical advantage in that the use of porous materials such as gels or phosphors as the "film" structure serves as the elemental capturing mechanism. Porous materials (gels, phosphors, etc.) can be added either as a discrete capturing medium (i.e., "deposited film") or fabricated as an integral (i.e., integrated) part of the free-standing resonant structure. Micro-optical structures such as spectroscopic gratings can be fabricated or etched into the porous materials themselves using ordinary processing techniques thereby resulting in a truly integrated structure with a tremendous reduction in cost and increase in performance and sensitivity (noise reduction in sampling/identification) due to the porous action as a micro-capillary device (elemental selectivity).

Yet another innovation provided by the present invention is the ability to heat the film/standing structure can be easily and/or inherently implemented in order to "purge" the structure on a repeated and controlled basis thereby allowing for repeated/scheduled usage and the generation of an inherently stable baseline for operation.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Figure 1:
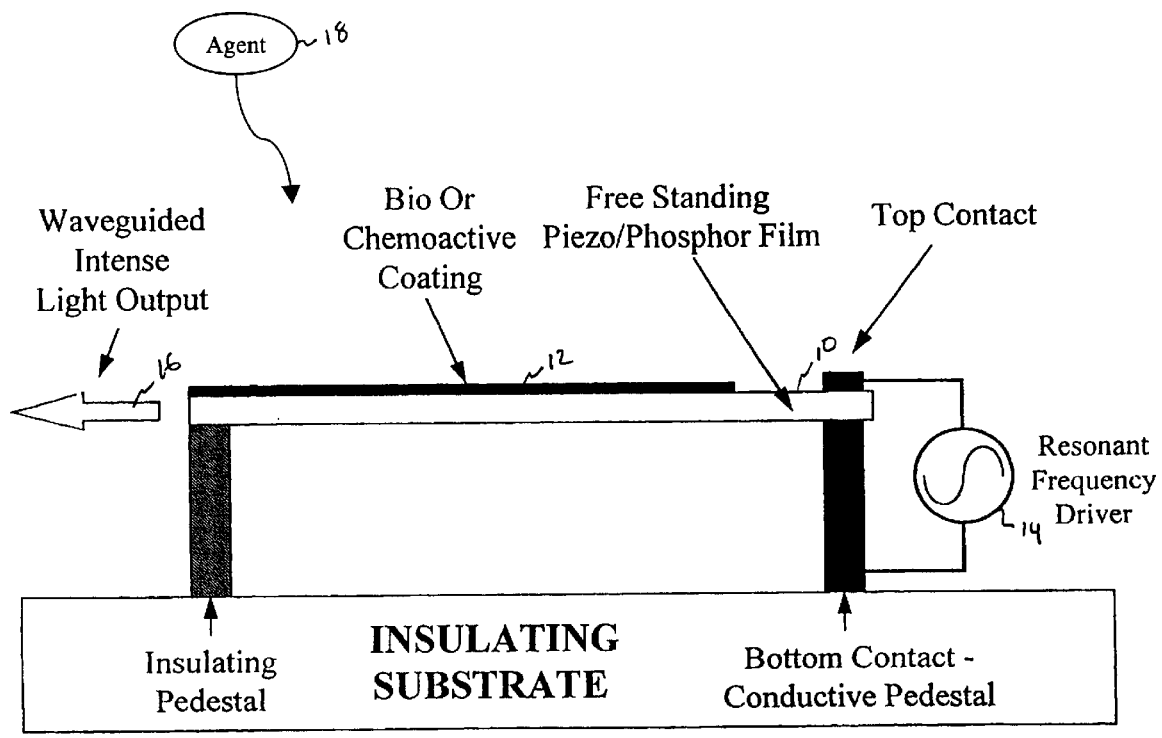
FIG. 1 illustrates one embodiment of the present invention.

Preferred embodiments of the present invention are illustrated in the FIGUREs, like numerals being used to refer to like and corresponding parts of the various drawings.

The present invention provides a real-time biological/chemical sensor based on changes in both the optical and resonance properties of a piezoelectric resonator consisting of a free standing thin film electroluminescent (EL) structure (including phosphors) due to absorption of biological or chemical agents on the surface of the resonant structure. The surface of the resonant structure can be treated to be chemically/biologically active for specific agents, and the EL properties of the resonator/phosphor/film combination will provide a simple, visual, real-time, and unambiguous identification of their presence. The sensor of the present invention may be small and inexpensive enough for distribution to personnel on an individual basis to alert them to possible exposure(s) and reactions and may also be used to aid subsequent medical personnel in their post-exposure treatment strategy and/or status monitorings.

Piezoelectric resonators have been used for many years as a sensor in thin film evaporation and sputtering systems to determine when the desired thickness or a real mass density of the film has been deposited. Typically this has been done by detecting the shift in its resonant frequency as the mass of the film or film material adds to the mass of the resonator. Quartz has been the usual choice for resonators due to its compatibility with high vacuum systems, its high resonance "Q" to accurately detect the small frequency shifts associated with nanometer thick depositions, and its high temperature compatibility with typical metal or ceramic deposition processes. With the advances in materials science over the past several decades, however, it is now known that there are also a variety of other materials which might also be considered for use in the proposed application.

A specific feature of piezoelectric resonators exploited by the present invention is the high surface voltage which can be developed when the resonators are driven at near-resonance using a much lower driving voltage. Experiments have shown that this high surface voltage can be used to directly excite luminescence in a variety of media in contact with, or in close proximity to the resonator surface. The effect was first reported in the UK for quartz resonators operated in a low pressure gas environment in which the surface voltages were high enough to produce luminous discharges in the gas just above the resonator's nodes. Excitation of EL phosphor powders by a surface acoustic wave on a piezoelectric crystal has also been openly reported. The high surface voltage produced by driving the resonator near resonance also serves as the basis for commercially available "solid-state transformers" which are an alternative to the typical wire-wound iron-core versions.

Many materials have piezoelectric properties, and among them are a number of common semiconductor and phosphor materials. Some EL phosphors as well as semiconductor materials such as silicon, have been investigated and developed as light sources, flat panel display elements, signs markers, etc.

Electroluminescent light sources can be made using specially prepared powder phosphors, and depending on their physical configuration, can be powered by either ac or dc in the low voltage/low current (down to 5 volts in some cases) range. One embodiment of the present invention specifically uses thin film phosphors and semiconductor materials similar to those used in flat panel displays for two main reasons. First, as a resonator, a free-standing thin film will be most sensitive to any changes in mass added to, or removed from its surface due to its own relatively low mass. Similarly, a free-standing thin film will more easily sense changes in the surface tension and/or viscosity of surface layers reacting with biological/chemical agents since the properties of the surface layers can be made a substantial part of the resonator properties itself. Second, because these free-standing thin films are fabricated as thin, transparent films, they also behave as optical waveguides thereby trapping the generated light in the film and concentrating the intensity of the generated light intensity at the edges. While this waveguiding effect has been a problem for thin film EL display manufacturers, the present invention uses this feature to enhance visual detectability and/or optoelectronic processor sensitivity.

Figure 2:
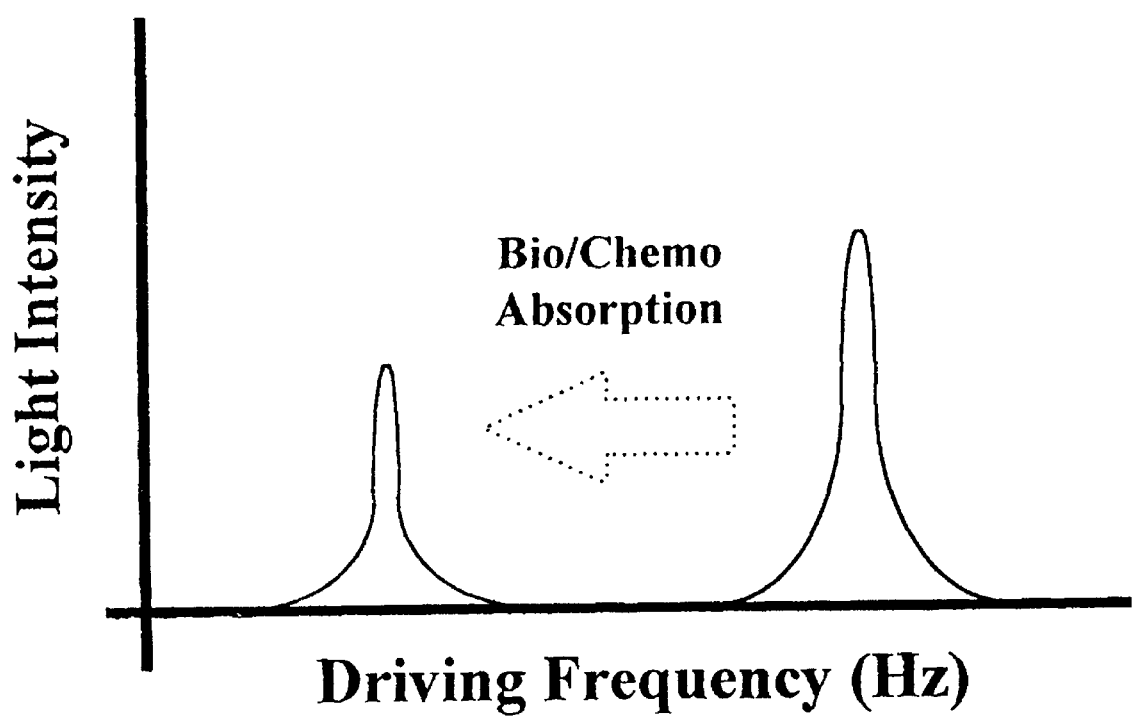
FIG. 2 depicts a change in the driving frequency of the present invention in the presence of biological and/or chemical agents.

FIG. 1 illustrates one embodiment of the present invention. This embodiment comprises a free-standing thin film EL phosphor 10 onto which a bio/chemo active surface layer 12 has been deposited. EL film 10 is electronically or mechanically excited to, or near resonance by frequency driver 14. The edge emitted light 16 intensity is measured. Upon exposure to the appropriate agent 18, surface layer 12 either increases in mass, decreases in mass, changes its surface tension, changes its viscosity, or other similar physical characteristic known to those skilled in the art, thus changing resonators 10 response to frequency driver 14. This change will be detected either as a change in the intensity of emitted light 16 or a shift in the driving frequency, as illustrated in FIG. 2, to achieve the same light intensity thereby indicating the presence of agent 15.

Other variations associated with the free-standing piezoelectric film may include changes in surface layer's 12 optical coupling to resonator 10 (e.g., through gratings or other optical structures fabricated on the free-standing film surface) thereby increasing/decreasing the amount of light scattered out of the flat surface of the thin film waveguide and/or providing the spectral content/signature of the emitted light/specimen.

Other design considerations such as the use of an atomic stylus or tip configuration as used in atomic force microscopes might be used in place of one or more of the pedestals 20 and 21 as shown to enhance/amplify the sensitivity of the sensor by an order of magnitude or more. Likewise, microsensors can be integrated directly onto the edges or surfaces where the signal or light emission 16 occurs in order to provide tremendous increases in the sensing capability as compared to a strictly visual sensing system.

Combinations of nanometer-micron thick phosphor and/or film stacks (including porous structures/materials) may also be used to provide a color discriminator between an uncontaminated and contaminated condition (e.g. green emission implies safe, but red emission implies danger).

The use of porous materials such as gels or phosphors as the illustrated "film" structure which serves as the elemental capturing mechanism. Porous materials (gels, phosphors, etc.) can be added either as a discrete capturing medium (i.e., "deposited film") or fabricated as an integral (i.e., integrated) part of the free-standing resonant structure.

Micro-optical structures such as spectroscopic gratings can be fabricated or etched into the porous materials themselves using ordinary processing techniques thereby resulting in a truly integrated structure with a tremendous reduction in cost and increase in performance and sensitivity (noise reduction in sampling/identification) due to the porous action as a micro-capillary device (elemental selectivity).

The ability to heat film 10 (standing structure) can be easily and/or inherently (e.g., reverse biasing) implemented (a particular benefit of porous materials) in order to "purge" the structure on a repeated and controlled basis thereby allowing for repeated/scheduled usage and the generation of an inherently stable baseline for operation.

The successful marriage of the mature electroluminescent (EL) and quartz resonator technologies into an integrated piezo-EL device is a completely innovative sensor technology in which sensed events are transmitted directly as high intensity optical signals via edge emission. Most sensors (and especially remote ones) require large power supplies to drive the sensor and local support electronics. This issue is only compounded if the sensor system is to be operational and functional on a remote-type basis where data transmission must also be included. Additional issues and complications are also introduced when in order to increase overall system sensitivities, the issues of susceptibility to all forms of external electromagnetic radiation and energies (interference) must also be solved in a reasonable way in order to provide or exhibit practicality on a routine basis.

The sensor system of the present invention requires substantially less power and exhibits an increase in robustness and practicality by utilizing the piezoelectric properties of the substrate materials themselves and/or to drive other sensor elements such as thin film electroluminescent (EL) stacks (either single layer or multiple layer). The present invention can transmit sensed events directly as a change in either the electronic signal (resonant) or as high intensity optical signals via edge emission. Detection can be achieved by a variety of mechanisms including radiation, chemical, acoustic, and seismic vibrational signals to quantitatively modulate the transmitted electronic and/or optical signals as illustrated in FIG. 2. Acoustic signals cause a change in luminescent output as a result of increased pressure on the piezoelectric driver substrate which alters its resonant frequency. A high intensity edge-emitting EL configuration can also be used as a light source for chemical- and radiation-sensitive filters whose transmissivity changes upon exposure where an event would be remotely detected as a change in intensity.

Figure 3:
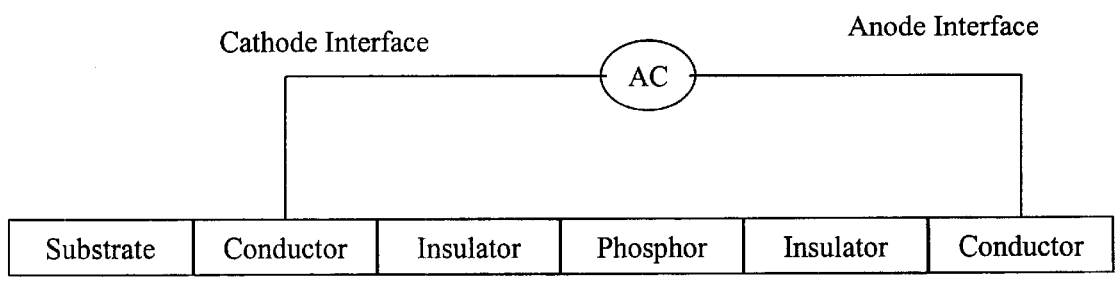
FIG. 3 illustrates one embodiment of an EL device of the present invention.

One embodiment uses direct converters that do not require large support electronics. A simple model describing these new devices is shown in FIG. 3. The devices as indicated are based on the use of a 10 angstrom to 1 micron thick phosphor film such as ZnS:Mn which offers very high luminance and efficiencies over a wide spectral range with common driving frequencies in the 1–10 MHz range and as high as 25 MHz.

The present invention may be fabricated by depositing thin film electroluminescent (EL) stacks (either single layer or multiple layer) directly onto piezoelectric driver substrates as illustrated in FIG. 3. In some cases the thin film EL might be limited by the transition or melting temperature of the piezoelectric substrate. In these instances, the limitations can be overcome by fabricating an inverted structure in which the EL layer or stack is deposited and processed completely prior to integration with the piezoelectric driver thereby enabling full optimization of the EL element for any piezoelectric driver material regardless of transition temperature.

It is also possible to also operate these structures in a free mode without direct integration onto a piezoelectric substrate such as quartz, etc. This use of the piezoelectric properties of the phosphor (ZnS:Mn) layer itself can be referred to as a self-driving piezo-EL device. This type of device can be fabricated using the "inverted" process described above, but bonded to a hollow support rather than a solid piezoelectric substrate.

In all of the above embodiments, the EL layers may be deposited in either the "closed" or tightly packed cell configuration, or the more "open" or loosely packed (porous) cell configuration. The porous EL stack configurations can, in many circumstances (chemical and vapor), act in a capillary fashion to further increase sensitivity, elemental discrimination or selectivity, as well as improve the process of elemental identification.

This invention discloses the integration of piezoelectric drivers and thin film EL devices for the first time into a new and innovative sensor device. The new devices utilize the very high voltage gains and high drive frequencies available from piezo drivers to dramatically increase luminescent output of the EL films.

The present invention also demonstrates the ability to enable full optimization of the EL element for any piezo driver material regardless of transition temperature (e.g., the "inverted" structures).

The invention also demonstrates the ability to design self-driving EL devices using common materials.

In summary, the present invention provides a system and method of using luminescent piezoelectric to detect biological and/or chemical agents.

The present invention provides a real-time luminescent piezoelectric detector capable of sensing the presence of biological and chemical agents. This detector includes a free-standing thin film that is driven by a frequency drover to produce light emitted from an edge of the thin film. A surface layer sensitive to the biological or chemical agent to be detected is disposed on the surface of the thin film. In the presence of the biological or chemical agent to be detected, the light emitted from the edge of the thin film structure is altered. A processor capable of determining the presence and/or concentration of the biological or chemical agent in question based on the altered emitted light receives an output representative of the emitted light and outputs the status of the presence and/or concentration of the biological or chemical agent in question.

Although the present invention has been described in detail, it should be understood that various changes, substitutions and alterations can be made hereto without departing from the spirit and scope of the invention as described by the appended claims.

What is claimed is:

1. A real-time luminescent piezoelectric detector to sense an agent, said detector comprising:
    a free-standing thin film structure;
    a surface layer deposited on said thin film structure said surface layer being adapted to interact with said agent;
    a frequency driver operable to drive said thin film structure at a frequency to cause said thin film structure to generate light, with the intensity of said light generated varying in response to said surface layer interacting with said agent; and
    an optical detection system operable to sense light generated by said thin film structure and produce a signal in response thereto.

2. The detector of claim 1, wherein said agent is selected from a set of agents consisting of biological agents and chemical agents.

3. The detector as recited in claim 1 wherein said surface layer is porous and further including a heater in thermal communication with said surface layer.

4. The detector of claim 1, further comprising a processor connected to receive said signal and produce output data representative of said agent.

5. The detector of claim 4, wherein said processor is operable to change said frequency of said frequency driver in order to maintain a constant intensity of said emitted light.

6. The detector of claim 1, wherein said free-standing thin film structure included an electroluminescent phosphor film.

7. The detector as recited in claim 6 wherein said optical detection system includes a microsensor integrated into said electroluminescent phosphor film.

8. The detector as recited in claim 6 wherein said free-standing thin film structure further includes two spaced-apart supports with said electroluminescent phosphor film extending therebetween, with one of said supports consisting of an atomic stylus.

9. The detector as recited in claim 6 wherein said electroluminescent thin film has gratings formed therein, facing said surface layer.

\* \* \* \* \*